US009364678B2

(12) United States Patent
Atanasoska et al.

(10) Patent No.: US 9,364,678 B2
(45) Date of Patent: *Jun. 14, 2016

(54) IMPLANTABLE ELECTRODES CONTAINING POLYOXOMETALATE ANIONS AND METHODS OF MANUFACTURE AND USE

(75) Inventors: Liliana Atanasoska, Edina, MN (US); Jan Weber, Maastricht (NL); Scott Schewe, Eden Prairie, MN (US); Robert W. Warner, Woodbury, MN (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 1038 days.

This patent is subject to a terminal disclaimer.

(21) Appl. No.: 13/166,528

(22) Filed: Jun. 22, 2011

(65) Prior Publication Data

US 2011/0251653 A1    Oct. 13, 2011

Related U.S. Application Data

(63) Continuation of application No. 11/614,870, filed on Dec. 21, 2006, now Pat. No. 7,991,483.

(51) Int. Cl.
*A61N 1/372* (2006.01)
*A61N 1/05* (2006.01)
*A61N 1/36* (2006.01)

(52) U.S. Cl.
CPC ............. *A61N 1/372* (2013.01); *A61N 1/0551* (2013.01); *A61N 1/05* (2013.01); *A61N 1/0553* (2013.01); *A61N 1/36* (2013.01); *A61N 1/37205* (2013.01)

(58) Field of Classification Search
CPC ... A61N 1/0551; A61N 1/0553; A61N 1/372; A61N 1/37205; A61N 1/05; A61N 1/36
See application file for complete search history.

(56) References Cited

U.S. PATENT DOCUMENTS

| 5,079,203 | A | | 1/1992 | Pinnavaia et al. |
| 5,193,539 | A | | 3/1993 | Schulman et al. |
| 5,193,540 | A | | 3/1993 | Schulman et al. |
| 5,312,439 | A | | 5/1994 | Loeb |
| 5,377,039 | A | * | 12/1994 | Babinec ................. 359/265 |
| 5,531,779 | A | | 7/1996 | Dahl et al. |
| 6,051,017 | A | | 4/2000 | Loeb et al. |
| 6,181,969 | B1 | | 1/2001 | Gord |
| 6,516,227 | B1 | | 2/2003 | Meadows et al. |

(Continued)

FOREIGN PATENT DOCUMENTS

| WO | 98/37926 | 9/1998 |
| WO | 98/43700 | 10/1998 |
| WO | 98/43701 | 10/1998 |

OTHER PUBLICATIONS

Kozhevnikov, I., "Catalysts for Fine Chemical Synthesis, vol. 2, Catalysis Polyoxometalates," Oct. 2002, 10 pages.

(Continued)

*Primary Examiner* — Niketa Patel
*Assistant Examiner* — Lindsey G Hankins
(74) *Attorney, Agent, or Firm* — Lowe Graham Jones PLLC; Bruce E. Black

(57) ABSTRACT

An implantable device includes at least one electrode comprising a conductive base and polyoxometalate anions disposed on or within the conductive base; and at least one conductor attached to the at least one electrode for conducting electrical energy to the at least one electrode.

20 Claims, 4 Drawing Sheets

(56) References Cited

U.S. PATENT DOCUMENTS

| | | | |
|---|---|---|---|
| 6,609,029 | B1 | 8/2003 | Mann et al. |
| 6,609,032 | B1 | 8/2003 | Woods et al. |
| 6,741,892 | B1 | 5/2004 | Meadows et al. |
| 6,911,470 | B1 | 6/2005 | Schinazi et al. |
| 6,914,029 | B2 | 7/2005 | Davis et al. |
| 7,244,150 | B1 | 7/2007 | Brase et al. |
| 7,672,734 | B2 | 3/2010 | Anderson et al. |
| 7,761,165 | B1 | 7/2010 | He et al. |
| 7,974,706 | B2 | 7/2011 | Moffitt et al. |
| 2004/0059392 | A1 | 3/2004 | Parramon et al. |
| 2005/0131496 | A1 | 6/2005 | Parramon et al. |
| 2005/0165301 | A1* | 7/2005 | Smith et al. .................. 600/421 |
| 2005/0222647 | A1* | 10/2005 | Wahlstrand et al. ............ 607/72 |
| 2006/0100696 | A1 | 5/2006 | Atanasoska et al. |
| 2006/0184092 | A1 | 8/2006 | Atanasoska et al. |
| 2006/0206162 | A1* | 9/2006 | Wahlstrand et al. ............ 607/46 |
| 2007/0150036 | A1 | 6/2007 | Anderson |
| 2007/0219595 | A1 | 9/2007 | He |
| 2007/0244569 | A1 | 10/2007 | Weber et al. |
| 2008/0071340 | A1 | 3/2008 | Atanasoska et al. |

OTHER PUBLICATIONS

White, A.M. et al., "Polymer Electrodes Doped with Heteropolymetallates and Their Use Within Solid-State Supercapacitors," Synthetic Metals, 139, 2003, pp. 123-131.

Xu, L. et al., "Towards Main-Chain-Polyoxometalate-Containing Hybrid Polymers: A Highly Efficient Approach to Bifunctionaiized Organoimido Derivatives of Hexamolybdates," Angew Chem., 114, 2002, pp. 4303-4306.

Mayer, C.R. et al., "New Hybrid Covalent Networks Based on Polyoxometalates: Part 1. Hybrid Newtworks Based on Poly(ethylmethacrylate) Chains Covalently Cross-linked by Heteropolyanions: Synthesis and Swelling Properties," Chemistry of Materials, vol. 12, No. 2, Feb. 2000, pp. 257-260.

Lu M. et al., "Synthesis of Main-Chain Polyoxometalate-Containing Hybrid Polymers and their applications in Photovoltaic Cells," Chem. Mater., 17, 2005, pp. 402-408.

Feng, Y. et al. "Fabrication and Characterization of Multilayer Films Based on Keggin-Type Polyoxometalate and Chitosan," Materials Letters, 60, 2006, pp. 1588-1593.

Roesner, R. A. et al., "Mono- and Di-functional Aromatic Amines With p-alkoxy Substituents as Novel Arylimido Ligands for the Hexamolybdate Ion," Inorganic Chemica Acta, 342, 2003, pp. 37-47.

Han, Z. et al., "Inorganic-Organic Hybrid Polyoxometalate Containing Supramolecular Helical Chains: Preparation, Characterization and Application in Chemically Bulk-Modified Electrode," Electrochemica Acta, 51, 2005, pp. 218-224.

Lan, Y. et al., "An Effective Layer-by-Layer Absorption and Polymerization Method to the Fabrication of Polyoxometalate-Polypyrrole Nanoparticle Ultrathin Films," Polymer, 47, 2006, 1480-1485.

Ding, B. et al., "Layer-by-Layer Self-Assembled Tubular Films Containing Polyoxometalate on Electrospun Nanofibers," Colloids and Surfaces A: Physicochem. En. Aspects, 284-85, 2006, pp. 257-262.

Yang, G. et al., "Modification of Electrode Surface Through Electrospinning Followed by Self-Assembly Multilayer Film of Polyoxometalate and its Photochromic," Electrochemistry Communications, 8, 2006, 790-796.

Kaba, M. S. et al., "Molecular Shapes, Orientation, and Packing of Polyoxometalate Arrays Imaged by Scanning Tunneling Microscopy," Inorg. Chem., 37, 2998, 398-406.

Sokan, O., "Power Sources for Implantable Medical Devices," Business Briefing: Medical Device Manufacturing & Technology, 2002, 4 pages.

Kan, Z. et al., "Synthesis and Characterization of Polyoxometalate Nanowires Based on a Novel Microemulsion Process," Nanotechnology, 15, 2004, pp. 55-58.

Xie, T., "Photoelectrochemical Reactivity of Polyoxophosphotungstates Embedded in Titania Tubules," Nanotechnology, 17, 2006, 3340-3346.

Gu, N. et al., "Study on Charge Transfer Reactions at Multilayers of Polyoxometalates Clusters and Poly(allylaminehydrochloride) (Grotthuss-018)" Electrochemica Acta, 51, 2006, pp. 6038-6044.

Fei, B. et al., "Ionic Peapods from Carbon Nanotubes and Phosphotungistic Acid," Carbon, 44, 2006 pp. 2261-2264.

Yang, Y. et al., "Efficient Degradation of Dye Pollutants on Nanoporoous Polyoxotungstate-Anatase Composite Under Visible-Light Irradiation," Journal of Molecular Catalysis A: Chemical, 225, 2005, pp. 203-212.

Wang, Y. et al., "Self-Assembled Multilayer Films Based on a Keggin-Type Polyoxometalate and Polyaniline," Journal of colloid and Interface Science, 264, 2005, pp. 176-183.

Gomez-Romero, P. et al., "Hybrid Organic-Inorganic Nanocomposite Materials for Application in Solid State Electrochemical Supercapacitors," Electrochemistry Communications, 5, 2003, pp. 149-153.

Official Communication for U.S. Appl. No. 11/614,870 mailed Sep. 28, 2009.

Official Communication for U.S. Appl. No. 11/614,870 mailed Apr. 12, 2010.

Official Communication for U.S. Appl. No. 11/614,870 mailed Dec. 30, 2010.

Official Communication for U.S. Appl. No. 11/614,870 mailed Apr. 4, 2011.

* cited by examiner

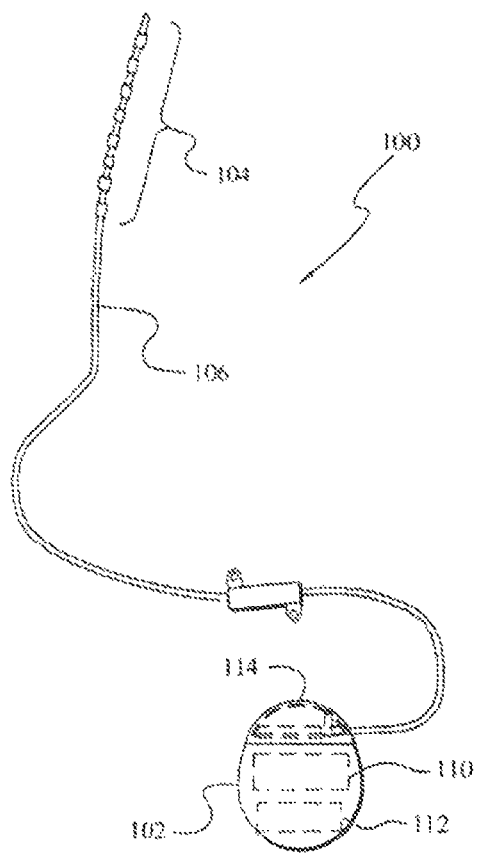
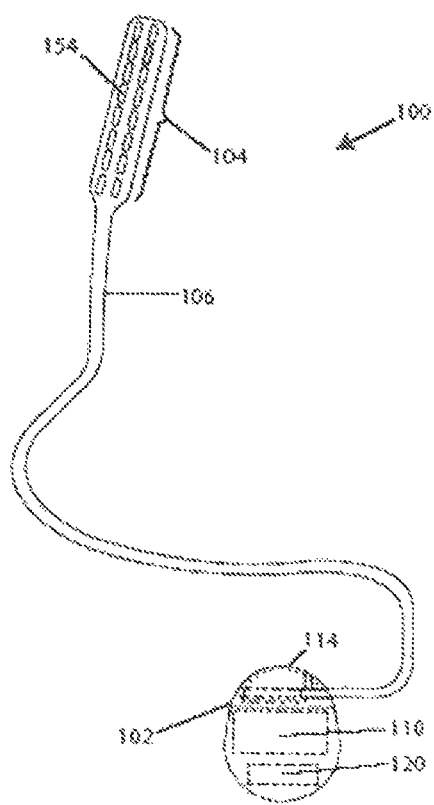
Figure 2
Figure 3

IMPLANTABLE ELECTRODES CONTAINING POLYOXOMETALATE ANIONS AND METHODS OF MANUFACTURE AND USE

CROSS-REFERENCE TO RELATED APPLICATIONS

This patent application is a continuation of U.S. Patent Application Serial No. 11/614,870 filed on Dec. 21, 2006, which is incorporated herein by reference.

FIELD

The invention is directed to implantable electrodes, devices that include the electrodes, and methods of manufacturing and using the electrodes and devices. In addition, the invention is directed to implantable electrodes with polyoxometalate anions, devices that include the electrodes, and methods of manufacturing and using the electrodes and devices.

BACKGROUND

Tissue stimulation using implantable electrodes has important therapeutic uses. For example, implantable pacemakers, defibrillators, and cardioverters stimulate the muscle tissue of the heart. Implantable neurostimulators have been developed to provide therapy for a variety of disorders, as well as other treatments. Implantable neurostimulators can be used in neurological therapy by stimulating nerves or muscles, for example, spinal cord tissue or brain tissue. Other uses of implantable neurostimulators include, but are not limited to, treatment for urinary or faecal urge incontinence by stimulating nerve fibers proximal to the pudendal nerves of the pelvic floor, treatment for erectile and other sexual dysfunctions by stimulating the cavernous nerve(s), treatment for reduction of pressure sores or venous stasis, etc. Other uses for implantable electrodes include muscle stimulation, gastroparesis treatment, wound healing, retinal and sub-retinal treatment, recording, sensing, and monitoring.

Stimulation systems typically include implantable electrodes attached to, or disposed adjacent to, the tissue to be stimulated. Some stimulation systems, including at least some spinal cord stimulation systems, have an implantable percutaneous, cuff, or paddle lead with multiple electrodes, as well as a separate control module that houses the power source and pulse generator. In many configurations, this control module is also implantable.

Implantable microstimulators, such as the BION® device (available from Advanced Bionics Corporation, Sylmar, Calif.), have exposed electrodes and a small, often cylindrical, housing that contains the electronic circuitry and power source that produce electrical pulses at the electrodes for stimulation of the neighboring tissue. Once implanted, it is often preferable that the microstimulator can be controlled and/or that the electrical source can be charged without removing the microstimulator from the implanted environment.

In many instances, implantable electrodes for electrical stimulation ideally should have a relatively small geometric surface area to produce a lower stimulation threshold and longer battery life. However, the reduction of the geometric surface area can increase current density and possibly exceed safe charge injection limits, which could result in, for example, dissolution of electrode material, undesirable electrolytic redox reductions, and production of toxic chemicals. This can be counteracted by increasing the actual surface area by, for example, using porous electrode materials such as platinized platinum, iridium oxide, titanium nitride, or sintered microspheres, or by using electrodes with fractal surface morphology or fractal coatings.

BRIEF SUMMARY

One embodiment is an implantable device that includes at least one electrode comprising a conductive base and polyoxometalate anions or their derivatives disposed on or within the conductive base; and at least one conductor attached to the at least one electrode for conducting electrical energy to the at least one electrode.

Another embodiment is a method of making an implantable electrode by forming a conductive base; and disposing polyoxometalate anions on or within the conductive base.

Yet another embodiment is a stimulation system that includes a housing; a power source disposed in the housing; at least one electrode comprising a conductive base and polyoxometalate anions disposed on or within the conductive base; and at least one conductor attached to the at least one electrode and to the power source to provide electrical energy to the at least one electrode.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 2 is a schematic top view of one embodiment of a stimulation system with a percutaneous electrode lead, according to the invention;

FIG. 3 is a schematic top view of one embodiment of a stimulation system with a paddle electrode lead, according to the invention;

DETAILED DESCRIPTION

Figures 1A, 1B:
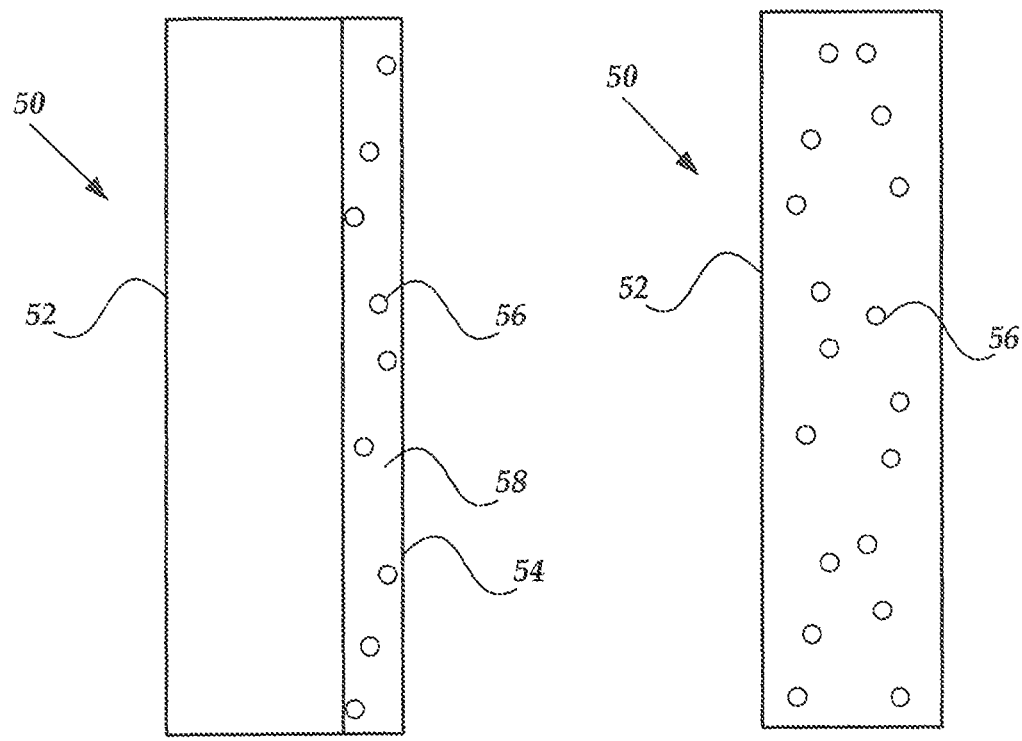
FIG. 1A is a schematic cross-sectional view of one embodiment of an implantable electrode, according to the invention.
FIG. 1B is a schematic cross-sectional view of a second embodiment of an implantable electrode, according to the invention.

The invention is directed to implantable electrodes, devices that include the electrodes, and methods of manufacturing and using the electrodes and devices. In addition, the invention is directed to implantable electrodes with polyoxometalate anions, devices that include the electrodes, and methods of manufacturing and using the electrodes and devices.

Suitable devices with implantable electrodes include, but are not limited to, therapeutic devices such as implantable pacemakers, defibrillators, cardioverters, neurostimulators, microstimulators, and muscle stimulators, all of which are electrostimulation device, as well as sensors and other diagnostic, monitoring and recording devices (for example, glucose sensors or seizure warning systems), controlled drug delivery systems, and therapeutic agent delivery systems. In some embodiments, the implantable device can include an electrode lead with one or more electrodes disposed on a distal end of the lead and one or more terminals disposed on a proximal end of the lead. Electrodes leads include, for example, percutaneous leads, cuff leads, and paddle leads. Examples of stimulation systems with electrode leads are described in, for example, U.S. Pat. Nos. 6,181,969; 6,516,227; 6,609,029; 6,609,032; and 6,741,892; and U.S. patent applications Ser. Nos. 11/238,240; 11/319,291; 11/327,880; 11/375,638; 11/393,991; and 11/396,309, all of which are incorporated herein by reference.

Examples of implantable microstimulators are described in U.S. Pat. Nos. 5,193,539; 5,193,540; 5,312,439; and 6,051,017; U.S. Patent Application Publication No. 2004/059392; U.S. patent application Ser. Nos. 11/040,209; 11/056,762; 11/084,368; and 11/238,240 and PCT Patent Applications Publication Nos. 98/37926; 98/43700; and 98/43701, all of which are incorporated herein by reference. The BION™ microstimulator, available from Advanced Bionics Corporation, Sylmar, Calif., is an example of a microstimulator.

The implantable electrode includes a conductive base and polyoxometalate anions, preferably as anion clusters, disposed on or within the conductive base. The polyoxometalate anions can be included, for example, in a coating, within the material of the conductive base, attached to the conductive base, or any combination thereof. For at least some embodiments, the implantable electrode with polyoxometalate anions can have improved capacitance, polarization, electrochemical performance, or stability (or any combination of these improvements) when compared to similar implantable electrodes without the polyoxometalate anions. The polyoxometalate anions may also significantly increase the number of surface sites for electrode materials or coatings.

The polyoxometalate anions can have the formula $[X_xM_yQ_wO_z]^{q-}$. M and Q are transition metals; X is a heteroatom and can be, for example, P, Si, B, Ge, As, S, Al or Sb; x, y, w, and z are integers where y and z are at least 5 and x and w may be 0; and q is an integer that represents the charge of the anion.

M and Q are preferably Ta, V, Mo, Co, Cr, Ni, Nb, W, Ti, Fe, Ir, Ru, Zr, Mn, Zn, Pd, Sn, Pt or Cu. More preferably, M is Mo, V, W, Nb, Ir, Zr, Fe, Ru, Ti, or Ta and even more preferably, M is Mo or W. More preferably, Q, if present, is Zn, Ti, Zr, Fe, Co, or Pd. X, if present, is preferably P, B, or Si. x is typically in the range of 0 to 8 and preferably in the range of 0 to 5. y is typically in the range of 5 to 30 and preferably in the range of 5 to 20. w is typically in the range of 0 to 12 and preferably in the range of 0 to 10. z is typically at least 10, preferably in the range of 10 to 80, and more preferably in the range of 18 to 62. q is typically in the range of 1 to 10 and preferably in the range of 1 to 6.

In addition, polyoxometalate anions include those in which one or more of the oxygen atoms are replaced with other covalently bonded substituents. Such polyoxometalate anions have the formula $[X_xM_yQ_wO_zR_r]^{q-}$ where R a covalently bonded substituent and r is an integer typically ranging from 0 to 10. Examples include, but are not limited to, organoimido derivatives such as those described in Xu, et al., Angew. Chem., 114, 4303-6 (2002); Roesner, et al., Inorganica Chimica Acta, 324, 34-47 (2003); and Lu, et al., Chem. Mater. 17, 402-408 (2005), all of which are incorporated herein by reference. In one embodiment, the organoimido substituent is $=NR^1$ where $R^1$ is substituted or unsubstituted aryl. The substituents on the aryl, if any, can be ortho-, para-, or meta-substituents (or any combination thereof if there are two or more substituents.) Examples of suitable substituents for the aryl moiety include, but are not limited to, alkyl, aralkyl, alkoxy, halo, hydroxy, alkenyl, alkynyl, nitro, cyano, amino, and the like. Any of these substituents may be substituted or unsubstituted.

Another example of the R substituent is $-Si-R^2$ as discussed, for example, in Mayer et al., Chem. Mater., 12, 257-60 (2000), incorporated herein by reference. $R^2$ can be any organic substituent including substituted or unsubstituted alkyl or aryl. In one embodiment, $R^2$ can be a monomeric unit that can be polymerized to form a cross-linked polymer network, such as a polymethacrylate (e.g., poly(ethyl methacrylate)) or polystyrene.

The polyoxometalate anions include, but are not limited to, those anions with the "Keggin" structure (examples: $(BW_{12}O_{40})^{5-}$ and $(SiW_{12}O_{40})^{4-}$) or "Dawson" structure (example: $(P_2W_{18}O_{62})^{6-}$). Other examples of structures include, but are not limited to, those discussed in Kaba, et al., Inorg. Chem. 37, 398-406 (1998), incorporated herein by reference. When x and w are 0, the anion ($[M_yO_z]^{q-}$) is sometimes referred to as an "isopoly" anion. When x≠0, the anion is sometimes referred to as a "heteropoly" anion.

Optionally, the polyoxometalate anions may also have one of more associated cations including, but not limited to, $H^+$, alkali metal cations, $NH_4^+$, alkaline earth cations, transition metal cations, and cationic organic compounds. Suitable cationic organic compounds include, for example, cationic polymers such as those with cationic monomer units, for example, polypyrrole, polythiophene, polyaniline, polyfurane, polyacetylene, chitosan, polyetherimide, and the like. The cationic organic compounds can also be non-polymeric. One example is the $Hbpy^+$ cation, where bpy is 2,4-bipyridine, as described, for example, in Han et al., Electrochimica Acta, 51, 218-224 (2005), incorporated herein by reference.

The polyoxometalate anions may also be formed on, or otherwise disposed on, a wire, fiber, or other object including, but not limited to, nanowires, nanofibers, and other nanoobjects.

For an implantable electrode, the polyoxometalate anions used in the electrode are preferably biocompatible. Such biocompatibility can take into account the expected length of time that the electrode is implanted, as well as the retention of the polyoxometalate anion, or constituents (e.g., atoms or ions) thereof, by the electrode over the implantation period.

FIG. 1A illustrates one embodiment of an implantable electrode 50. The implantable electrode includes a conductive base 52 and a coating 54. The conductive base can be any biocompatible, conductive material including, but not limited to, metals, alloys, metal oxides, metal nitrides, metal carbides, metal borides, carbon, doped silicon, and conductive polymers (including polymers with conductive fillers), as well as any combinations thereof. The conductive base may be, for example, a unitary body or can contain multiple conductive layers.

The coating 54 includes the polyoxometalate anions 56 and a carrier 58. The polyoxometalate anions are typically dispersed within the carrier. The polyoxometalate anions can be uniformly or non-uniformly dispersed within the carrier. The polyoxometalate anions may all have the same chemical composition or anions with two or more different chemical compositions can be used together.

The carrier 58 is preferably a biocompatible, conductive material such as a conductive polymer, polyelectrolyte, ionomer, polymer-ceramic hybrid (and other inorganic-organic hybrids), or conductive ceramic (e.g., iridium oxide or ruthenium oxide, as well as other conductive oxides, conductive nitrides, or mixtures thereof), or any combination thereof. Preferably, the conductive material can form cationic sites. Examples of suitable conductive polymer materials include, but are not limited to, polypyrrole, polythiophene, polyaniline, polyfurane, polyacetylene, cationic polyelectrolytes, polyetherimide (PEI), poly(diallyldimethlyammonium chloride) (PDDA), poly(allylamine hydrochloride) (PAH), chitosan, polylysine, and the like.

The coating 54 can be formed in any manner including by depositing the carrier and polyoxometalate anions onto the conductive base using any coating or deposition method such as, for example, dip coating, drip coating, spin coating, curtain coating, electropolymerization, layer-by-layer coating alternating between the carrier and the polyoxometalate anions, Langmuir-Blodget films, sol-gel, self assembly, electro-spraying, magneto-electrophoresis, or any other coating method. In some embodiments, the carrier is a polymeric material formed using monomer materials that are polymerized prior to, or after deposition, on the conductive base. The polyoxometalate anions can be incorporated into the coating prior to, during, or after polymerization. In one embodiment, the monomer material is disposed on the conductive base with the polyoxometalate anions and the monomer material is then polymerized using any polymerization technique including, but not limited to, electrochemical polymerization, vapor growth, or plasma polymerization. In another embodiment, the polymer is formed prior to deposition on the conductive base.

In other embodiments, the polyoxometalate anions can be doped into an already formed coating using any technique. Examples of suitable techniques include, but are not limited to, diffusion techniques and acid-base doping techniques.

The coating may also include one or more additives. Examples of additives include fillers, colorants, anti-oxidants, plasticizers, accelerants, initiators, nanoparticles, therapeutic agents, biomolecules, and the like.

Any suitable coating thickness can be used. For example, the coating can have a thickness in the range of 0.5 to 15 micrometers.

The level of polyoxometalate anions in the coating can be selected to provide desired properties. For example, in some embodiments, the polyoxometalate anions may be up to 40 wt. % of the coating (although it will be understood that other embodiments may include even more of the polyoxometalate anions). In at least some embodiments, the polyoxometalate anions may be in the range of 5 wt. % to 40 wt. % of the coating. In at least some embodiments using a polymeric carrier, the ratio of carrier monomers to polyoxometalate anions is at least 10:1 and may be in the range of 4:1 to 1:1.

Physical, electrical, and chemical characteristics of the coating 54 and implantable electrode 50 can be controlled or modified by a variety of factors including, but not limited to, the selection of particular polyoxometalate anion(s) or derivative(s) thereof and carrier, the level of polyoxometalate anions in the coating, the relative thickness of the coating, and the use of additives. For example, electrical characteristics such as, for example, capacitance, impedance, charge transfer resistance, or faradaic resistance, can be controlled or modified by selecting the chemical composition and doping level of the polyoxometalate anions. In some embodiments, the level of polyoxometalate anions in the coating can be adjusted by co-doping with other anions.

FIG. 1B illustrates another implantable electrode 50 with polyoxometalate anions 56 dispersed in the material of the conductive base 52. The anions can be uniformly or non-uniformly dispersed in the conductive base.

Polyoxometalate anions can be included with the formation of the conductive base 52. For example, the polyoxometalate anions can be included as the conductive base is formed. Examples of suitable techniques for forming the conductive base with polyoxometalate anions include, but are not limited to, sputtering, electrodeposition, sol-gel formation, co-deposition, self-assembly, ion-implantation, or multilayer deposition (with individual layers of polyoxometalate anions and conductive base). Examples of suitable materials for the sol-gel formation of a conductive base include, but are not limited to, $IrO_2$, $TiO_2$—$IrO_2$, $IrO_2$—$TaO_2$, platinized platinum, Pt, Pt—Ir, TiN, carbon, silicon, $RuO_2$ and the like. In other embodiments, the polyoxometalate anions can be incorporated into the conductive base after it is formed using, for example, diffusion and acid-base doping techniques.

Physical, electrical, and chemical characteristics of the implantable electrode 50 can be controlled or modified by a variety of factors including, but not limited to, the selection of particular polyoxometalate anion(s) and carrier and the level of polyoxometalate anions in the conductive base.

Figure 1C:
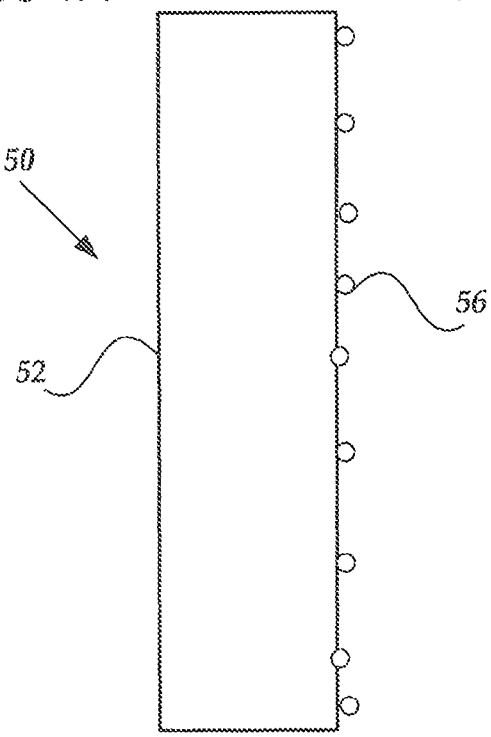
FIG. 1C is a schematic cross-sectional view of a third embodiment of an implantable electrode, according to the invention.

FIG. 1C illustrates another implantable electrode 50 with polyoxometalate anions attached to the material of the conductive base 52. The polyoxometalate anions can be, for example, pendant surface ligands attached via ionic or covalent bonds or any combination thereof. In some embodiments, the surface of the conductive base 52 may be prepared for attachment of the polyoxometalate anions. For example, the surface may be chemically or mechanically treated to produce radicals on the surface. In some embodiments, the conductive base may be a multilayer construction with the top layer being selected or prepared for attachment of the polyoxometalate anions.

Physical, electrical, and chemical characteristics of the implantable electrode 50 can be controlled or modified by a variety of factors including, but not limited to, the selection of particular polyoxometalate anion(s) and carrier and the level of polyoxometalate anions attached to the conductive base.

It will be understood that the embodiments illustrated in FIGS. 1A, 1B, and 1C can be combined together in any combination. For example, the implantable electrode may have polyoxometalate anions disposed in the conductive base and in a coating on the conductive base.

FIGS. 2 and 3 illustrate schematically embodiments of a stimulation system 100 that includes a control module (e.g., a stimulator or pulse generator) 102, an array body 104, and at least one lead body 106 coupling the control module to the electrode array. The array body 104 and the lead body 106 form a lead. In FIG. 2 the lead is a percutaneous lead and in FIG. 3 the lead is a paddle lead. It will be understood that the stimulation system for can include more, fewer, or different components and can have a variety of different configurations including those configurations disclosed in the references cited herein. The stimulation system or selected components of the stimulation system, including one or more of the lead body 106, the array body 104 and the control module 102, can be implanted into the body.

The array body 104 includes multiple implantable electrodes 154. One or more of the implantable electrodes 154 include polyoxometalate anions as described above. In some embodiments, all of the implantable electrodes include polyoxometalate anions.

A conductor (not shown) is attached to each of the electrodes 154 and extends along the lead body 106 to the control module 102 to conduct electrical pulses from the control module to the electrode. Preferably, the conductor is attached to the back side of the electrode 154, which is the side of the electrode 154 opposite the side that will be exposed to the body tissue. The conductors can be made of any conductive material. Examples of suitable material for conductors include, for example, metals, alloys, conductive polymers, and conductive carbon. In one embodiment, the conductors are insulated by an insulating material except where the conductor makes contact with the electrode 154. The insulating material may be any material that is a poor conductor of an electrical signal, including, for example, Teflon™, non-conductive polymers, nylon, Mylar, polyether bloc amides (such as the PEBAX™ resins available from Arkema, Inc., Philadelphia, Pa.), polytetrafluoroethylene (PTFE), polyimide, polyurethane, and composite materials. The conductors may be attached to the electrodes by any method including, for example, resistance welding, laser welding, conductive epoxy, and the like. Preferably, the conductors are attached to the electrodes 154 by a method that results in a durable attachment of the conductors to the electrodes 154 under expected usage conditions.

The lead body 106 and array body 104 (excluding the electrodes 154) are typically made of a non-conductive material such as, for example, silicone, polyurethane, polyetheretherketone (PEEK), epoxy, and the like. Optionally, the lead body may include one or more lumens through which the conductors pass or through which a drug or other medication can pass to the site of stimulation near the electrodes 154. The lead body 106 also may include a connector (not shown) for attachment to the control module 102 with contacts to connect the conductors to corresponding contacts of the control module.

The control module 102 typically includes a housing 114 with an electronic subassembly 110 and, in at least some embodiments, a power source 112 disposed within a chamber in the housing. Preferably, the housing is resistant to moisture penetration into the chamber containing the electronic subassembly and power source. In some embodiments, water may diffuse through the housing. Preferably, the diffused water is relatively pure, without substantial ionic content, as deionized water is relatively non-conductive. The housing 114 may be made of any biocompatible material including, for example, glass, ceramics, metals, polymers, and combinations thereof. The thickness of the walls of the housing may also impact the moisture permeability of the housing. A minimum thickness needed to achieve a particular degree of resistance to moisture transport will often depend on the material selected for the housing, as well as any additives.

Optionally, the housing 114 can be covered, in full or in part, with a coating. The coating can be provided to improve or alter one or more properties of the housing 114 including, for example, biocompatibility, hydrophobicity, moisture permeability, leaching of material into or out of the housing, and the like. In one embodiment, a coating can be applied which contains a compound, such as, for example, a drug, prodrug, hormone, or other bioactive molecule, that can be released over time when the stimulator is implanted. In another embodiment, the housing itself may include such a compound to be released over time after implantation.

Figure 4:
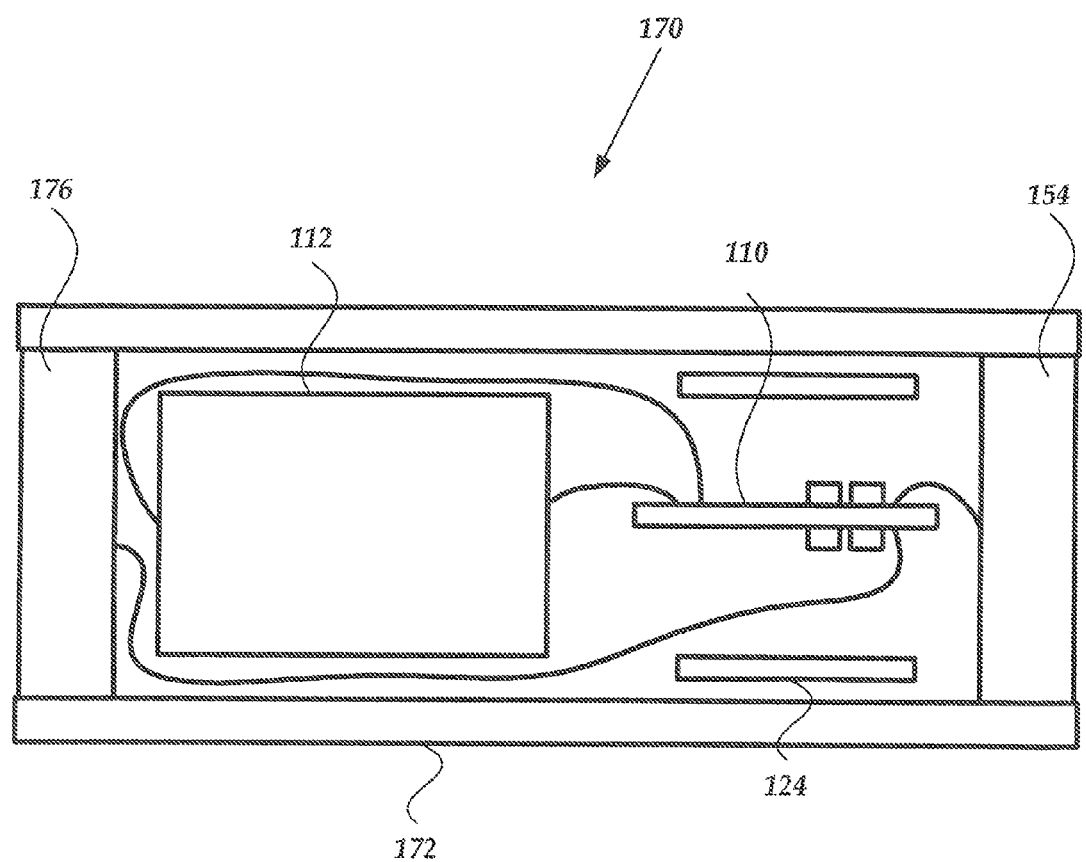
FIG. 4 view of one embodiment of a microstimulator, according to the invention.

FIG. 4 illustrates one embodiment of an implantable microstimulator 170. The implantable microstimulator 170 includes a housing 172, an implantable electrode 154 that contains polyoxometalate anions, an optional second electrode 176 (which may or may not contain polyoxometalate anions), a power source 112, an electronics subassembly 110, and an optional antenna 124. Other embodiments of an implantable microstimulator may include more or fewer components. It will be understood that the power source 112 and/or components of the electronics subassembly 110 and/or the optional antenna 124 can be provided outside of the housing in a separate unit and coupled to the implantable microstimulator by a lead.

The housing 172 can be formed of any material that resists the transport of moisture into the interior of the housing and is sufficiently sturdy to protect the components in the interior of the housing from damage under expected implantation and usage conditions. Suitable materials for the housing 172 (or a portion of the housing) include, for example, metals, ceramics, glass, plastics, and combinations thereof. The housing of the microstimulator is preferably composed of biocompatible materials.

Optionally, the housing 172 can be covered, in full or in part, with a coating. The coating can be provided to improve or alter one or more properties of the housing including, for example, biocompatibility, hydrophobicity, conductivity, moisture permeability, leaching of material into or out of the housing, and the like. The optional coating can be a polymer material, inorganic material, or organic material. As an example, a silicone coating may be used to improve biocompatibility. In yet another example, a coating can be applied which contains a compound, such as, for example, a drug, prodrug, hormone, or other bioactive molecule, that can be released over time when the microstimulator is implanted.

In at least some embodiments, the length of the microstimulator is no greater than 30 mm. Typically the length of the microstimulator is in the range of 10 to 30 mm.

The microstimulator can be implanted into the body tissue using a variety of methods including surgical methods. In some embodiments, the implantable electrode can be implanted using a hypodermic needle or other insertion cannula. Examples of insertion techniques can be found in U.S. Pat. No. 6,051,017.

Figure 5:
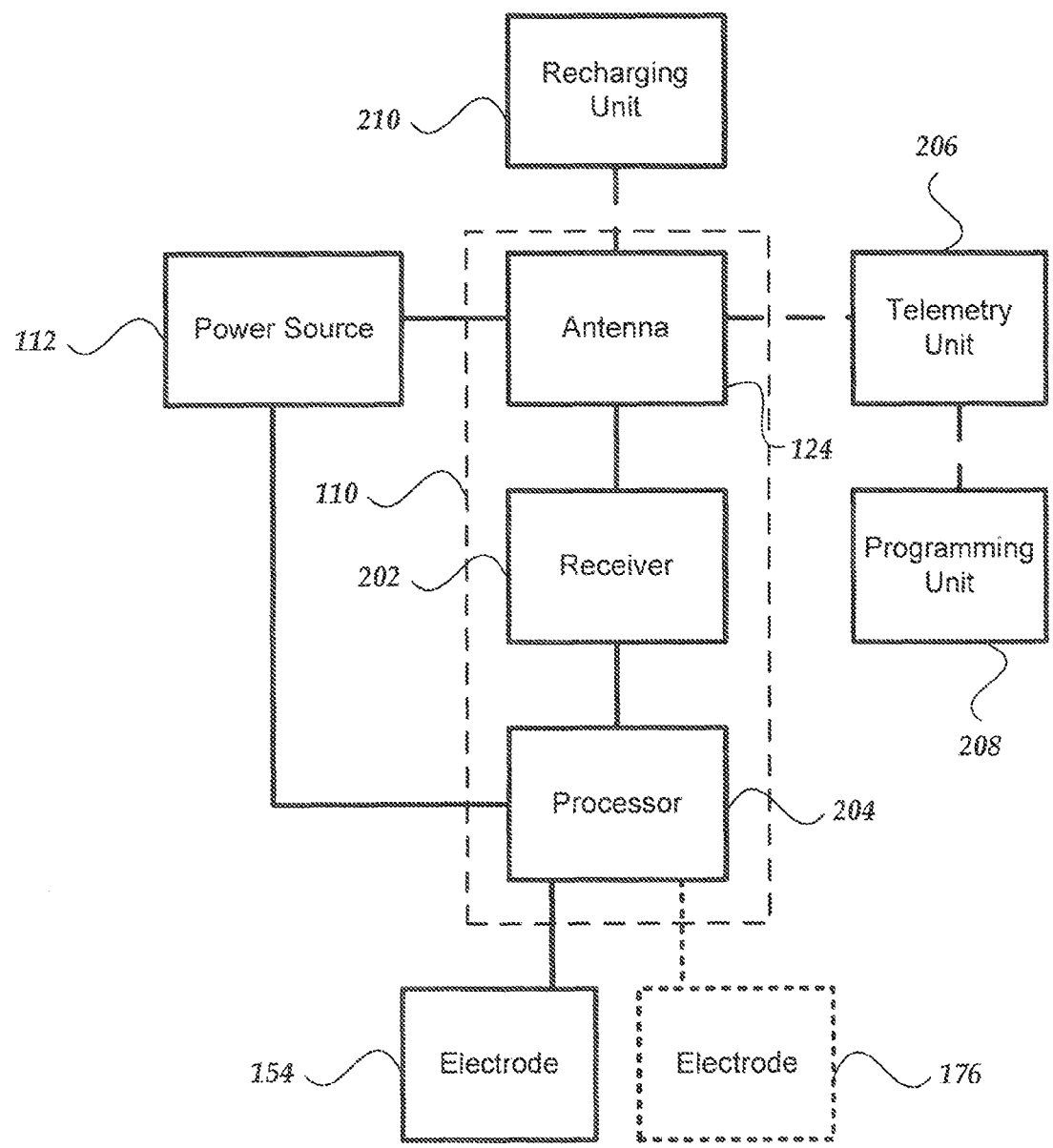
FIG. 5 is a schematic block diagram of components for one embodiment of a stimulation system, according to the invention.

FIG. 5 is a schematic overview of one embodiment of components of a system for stimulation (for example, the stimulation systems of FIGS. 2 and 3 or the microstimulator of FIG. 4), including an electronic subassembly 110 (which may or may not include the power source 112), according to the invention. It will be understood that the system for stimulation and the electronic subassembly 110 can include more, fewer, or different components and can have a variety of different configurations including those configurations disclosed in the stimulator references cited herein. Some or all of the components of the system for stimulation can be positioned on one or more circuit boards or similar carriers within a housing of a stimulator, if desired.

Any power source 112 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Patent Application Publication No. 2004/0059392, incorporated herein by reference.

As another alternative, power can be supplied by an external power source through inductive coupling via the optional antenna 124 or a secondary antenna. The external power source can be in a device that is mounted on the skin of the user or in a unit that is provided near the stimulator user on a permanent or periodic basis.

If the power source 112 is a rechargeable battery, the battery may be recharged using the optional antenna 124, if desired. Power can be provided to the battery 112 for recharging by inductively coupling the battery through the antenna to a recharging unit 210 external to the user. Examples of such arrangements can be found in the stimulator references identified above.

In one embodiment, electrical current is emitted by the electrodes 154 (and 176) to stimulate, for example, motor nerve fibers, muscle fibers, or other body tissues near the stimulator. The electronic subassembly 110 provides the electronics used to operate the stimulator and generate the electrical pulses at the electrodes 154 (and 176) to produce stimulation of the body tissues.

In the illustrated embodiment, a processor 204 is generally included in the electronic subassembly 110 to control the timing and electrical characteristics of the stimulator. For example, the processor can, if desired, control one or more of the timing, frequency, strength, duration, and waveform of the pulses. In addition, the processor 204 can select which electrodes can be used to provide stimulation, if desired. In some embodiments, the processor may select which electrode(s) are cathodes and which electrode(s) are anodes. This process may be performed using an external programming unit, as described below, that is in communication with the processor 204.

Any processor can be used. For example, the processor can be as simple as an electronic device that produces pulses at a regular interval or the processor can be complex and capable of receiving and interpreting instructions from an external programming unit 208 that allow modification of pulse characteristics. In the illustrated embodiment, the processor 204 is coupled to a receiver 202 which, in turn, is coupled to the optional antenna 124. This allows the processor to receive instructions from an external source to direct the pulse characteristics and the selection of electrodes, if desired.

In one embodiment, the antenna 124 is capable of receiving signals (e.g., RF signals) from an external telemetry unit 206 which is programmed by a programming unit 208. The programming unit 208 can be external to, or part of, the telemetry unit 206. The telemetry unit 206 can be a device that is worn on the skin of the user or can be carried by the user and can have a form similar to a pager or cellular phone, if desired. As another alternative, the telemetry unit may not be worn or carried by the user but may only be available at a home station or at a clinician's office. The programming unit 208 can be any unit that can provide information to the telemetry unit for transmission to the stimulator. The programming unit 208 can be part of the telemetry unit 206 or can provide signals or information to the telemetry unit via a wireless or wired connection. One example of a suitable programming unit is a computer operated by the user or clinician to send signals to the telemetry unit.

The signals sent to the processor 204 via the antenna 124 and receiver 202 can be used to modify or otherwise direct the operation of the stimulator. For example, the signals may be used to modify the pulses of the stimulator such as modifying one or more of pulse duration, pulse frequency, pulse waveform, and pulse strength. The signals may also direct the stimulator to cease operation or to start operation or to start charging the battery. In other embodiments, the electronic subassembly 110 does not include an antenna 124 or receiver 202 and the processor operates as programmed.

Optionally, the stimulator may include a transmitter (not shown) coupled to the processor and antenna for transmitting signals back to the telemetry unit 206 or another unit capable of receiving the signals. For example, the stimulator may transmit signals indicating whether the stimulator is operating properly or not or indicating when the battery needs to be charged. The processor may also be capable of transmitting information about the pulse characteristics so that a user or clinician can determine or verify the characteristics.

The optional antenna 124 can have any form. In one embodiment, the antenna comprises a coiled wire that is wrapped at least partially around the electronic subassembly within or on the housing.

The above specification, examples and data provide a description of the manufacture and use of the composition of the invention. Since many embodiments of the invention can be made without departing from the spirit and scope of the invention, the invention also resides in the claims hereinafter appended.

What is claimed and desired to be protected by Letters Patent of the United States is:

1. An implantable lead, comprising:
   an elongate lead body comprising a distal portion and a proximal portion;
   a plurality of electrodes disposed on the distal portion of the lead body, at least one of the electrodes comprising a conductive base and polyoxometalate anions disposed on or within the conductive base, wherein the polyoxometalate anions comprise anions having the formula $[X_xM_yQ_wO_z]^{q-}$ or the formula $[X_xM_yQ_wO_zR_r]^{q-}$ wherein M and Q are independently selected from Ta, V, Mo, Co, Cr, Ni, Nb, W, Ti, Fe, Ir, Ru, Zr, Mn, Zn, Pd, Sn, Pt, or Cu; X is selected from P, Si, B, Ge, As, or Sb; R is a covalently bonded substituent; x, y, w, z, and r are integers, wherein y and z are at least 5 and x, w, and r are at least 0; and q is an integer that represents the charge of the anion; and
   a plurality of conductors disposed in the lead body and attached to the plurality of electrodes for conducting electrical energy to the plurality of electrodes for stimulation of adjacent tissue when implanted.

2. The implantable lead of claim 1, wherein the lead is a percutaneous lead with the plurality of electrodes arranged sequentially along the distal portion of the lead body.

3. The implantable lead of claim 1, wherein the lead is a paddle lead comprising an array body at the distal portion of the lead body, wherein the plurality of electrodes are arranged as an array on the array body.

4. The implantable lead of claim 1, further comprising a coating disposed on the conductive base, wherein at least a portion of the polyoxometalate anions are dispersed in the coating.

5. The implantable lead of claim 4, wherein the coating comprises a conductive polymer carrier within which the portion of the polyoxometalate anions are dispersed.

6. The implantable lead of claim 5, wherein the conductive polymer carrier is selected from polypyrrole, polythiophene, polyaniline, polyfurane, polyacetylene, polyetherimide, poly (diallyldimethylammonium chloride), poly(allylamine hydrochloride), chitosan, or polylysine.

7. The implantable lead of claim 1, wherein at least a portion of the polyoxometalate anions are dispersed within the conductive base.

8. The implantable lead of claim 1, wherein at least a portion of the polyoxometalate anions are attached to a surface of the conductive base.

9. The implantable lead of claim 1, wherein each of the electrodes comprises the conductive base and the polyoxometalate anions.

10. The implantable lead of claim 1, wherein the plurality of electrodes form an array.

11. A method of stimulating tissue, the method comprising:
    implanting an electrode into tissue, the electrode comprising a conductive base and polyoxometalate anions disposed on or within the conductive base, wherein the polyoxometalate anions comprise anions having the formula $[X_xM_yQ_wO_z]^{q-}$ or the formula $[X_xM_yQ_wO_r]^{q-}$ wherein M and Q are independently selected from Ta, V, Mo, Co, Cr, Ni, Nb, W, Ti, Fe, Ir, Ru, Zr, Mn, Zn, Pd, Sn, Pt, or Cu; X is selected from P, Si, B, Ge, As, or Sb; R is a covalently bonded substituent; x, y, w, z, and r are integers, wherein y and z are at least 5 and x, w, and r are at least 0; and q is an integer that represents the charge of the anion;

coupling the electrode to a power source and an electronic subassembly configured and arranged to control delivery of electrical energy from the power source to the electrode; and delivering electrical energy from the power source to the electrode to stimulate the tissue.

12. The method of claim 11, wherein the electrode is disposed on an implantable lead, wherein implanting the electrode into tissue comprises implanting the implantable lead with the electrode into tissue.

13. The method of claim 11, wherein a control module comprises the power source and the electronic subassembly.

14. The method of claim 13, further comprising implanting the control module.

15. The method of claim 11, wherein a microstimulator comprises the electrode, the power source, and the electronic subassembly, wherein implanting the electrode into tissue comprises implanting the microstimulator into tissue.

16. An impiantabie electrode, comprising:
a conductive base; and
polyoxometalate anions disposed on or within the conductive base, wherein the polyoxometalate anions comprise anions having the formula $[X_xM_yQ_wO_z]^{q-}$ or the formula $[X_xM_yQ_wO_zR_r]^{q-}$ wherein M and Q are independently selected from Ta, V, Mo, Co, Cr, Ni, Nb, W, Ti, Fe, It, Ru, Zr, Mn, Zn, Pd, Sn, Pt, or Cu; X is selected from P, Si, B, Ge, As, or Sb; R is a covalently bonded substituent; x, y, w, z, and r are integers, wherein y and z are at least 5 and x, w, and r are at least 0; and q is an integer that represents the charge of the anion;
wherein the electrode is configured and arranged for implantation into a patient for delivery of electrical stimulation to tissue of the patient adjacent the electrode.

17. The electrode of claim 16, further comprising a coating disposed on the conductive base, wherein at least a portion of the polyoxometalate anions are dispersed in the coating.

18. The electrode of claim 17, wherein the coating comprises a conductive polymer carrier within which the portion of the polyoxometalate anions are dispersed.

19. The electrode of claim 16, wherein at least a portion of the polyoxometalate anions are dispersed within the conductive base.

20. The electrode of claim 16, wherein at least a portion of the polyoxemetalate anions are attached to a surface of the conductive base.

* * * * *